United States Patent [19]
Rijkers et al.

[11] Patent Number: 5,637,754
[45] Date of Patent: Jun. 10, 1997

[54] CRYSTALLIZATION OF α-L-ASPARTYL-L-PHENYLALANINE METHYL ESTER FROM AQUEOUS SOLUTION

[75] Inventors: Marinus P. W. M. Rijkers, Stein; Antoon G. T. Toussaint, Heerlen; Alexander P. M. Vrinzen, Meerssen, all of Netherlands

[73] Assignee: Holland Sweetener Co., V.o.F., Maastricht, Netherlands

[21] Appl. No.: 575,713

[22] Filed: Dec. 20, 1995

[30] Foreign Application Priority Data

Dec. 22, 1994 [EP] European Pat. Off. .............. 94203726

[51] Int. Cl.$^6$ ................................................. C07C 229/02
[52] U.S. Cl. .................................................... 560/41
[58] Field of Search ............................................ 560/41

[56] References Cited

U.S. PATENT DOCUMENTS 4,962,222  10/1990  Mita et al. .

OTHER PUBLICATIONS

European Search Report, Document No. EP 94 20 3726 dated May 30, 1995.

*Primary Examiner*—Samuel Barts
*Attorney, Agent, or Firm*—Cushman Darby & Cushman IP Group of Pillsbury Madison & Sutro, LLP

[57] ABSTRACT

A method for crystallizing aspartame comprising the combination of steps of: (A) providing (i) dispersed droplets of a fluid mixture comprising aspartame and water, and (ii) a water-immiscible fluid zone; (B) passing the dispersed droplets through the water-immiscible fluid zone under effective temperature and dispersive conditions to effect cooling of the dispersed droplets so that a state of initial relative supersaturation of aspartame between about 1 and 6 is formed within the dispersed droplets; (C) collecting the dispersed droplets in the supersaturated state in a substantially static collection zone so that a slurry comprising a crystalline form of aspartame is formed from the droplets. The method provides for rapid, efficient cooling of aspartame solutions and yields aspartame crystals with desirable qualities.

22 Claims, 1 Drawing Sheet

CRYSTALLIZATION OF α-L-ASPARTYL-L-PHENYLALANINE METHYL ESTER FROM AQUEOUS SOLUTION

BACKGROUND OF THE INVENTION

1. Field of the invention

The invention relates to a method for crystallizing a-L-aspartyl-L-phenylalanine methyl ester (aspartame), and more particularly, to a method for crystallizing aspartame by passing dispersed droplets comprising water and aspartame through water-immiscible fluids to generate a state of initial relative supersaturation within the dispersed droplets.

2. Description of the Related Art

Aspartame is the a-dipeptide ester L-aspartyl-L-phenylalanine methyl ester ("APM"). As an important synthetic low-calorie sweetening agent, aspartame is about 200 times as sweet as sugar with an exceptionally good taste pattern, but without a bitter aftertaste. This sweetener is used in a wide range of products such as soft drinks, sweets, table-top sweeteners, pharmaceutical products, and the like.

Aspartame can be prepared by several routes. One route, for example, involves the chemical coupling of N-protected L-aspartic acid or the anhydride thereof and (L-) phenylalanine or the methyl ester thereof. The protecting group is optionally removed later, and aspartame can be obtained by esterification if still necessary. Examples of such a process are disclosed in, for example, U.S. Pat. No. 3,786,039, the complete disclosure of which is hereby incorporated by reference. In processes for the preparation of aspartame by chemical coupling, relatively large amounts of β-APM are usually formed as a side-product. Work-up of the desired α-APM often occurs through formation of, for example, the APM.HCl-salt followed by neutralization crystallization. Such methods inevitably lead to the production of large amounts of inorganic salt.

There also exist enzymatic processes for the production of aspartame, whereby, for instance, N-protected L-aspartic acid and (DL-)-phenylalanine methyl ester are selectively coupled to form the LL-α-dipeptide derivative, which is subsequently converted to aspartame. Such a process is described in, for example, U.S. Pat. No. 4,116,768, the complete disclosure of which is hereby incorporated by reference.

In any aspartame production process, one of the final process steps is to obtain aspartame in crystalline form from the solvent in which it is present. However, reaction by-products and/or decomposition products are also present. Usually, the solvent is an aqueous solvent. An aqueous solvent can be either water or a mixed solvent of water and up to about 25% (wt.) of a water-miscible organic solvent such as, for example, a lower alcohol having one to three carbon atoms. As used hereinafter, the term aqueous encompasses either water or water containing up to about 25% (wt.) of a $C_{1-3}$ alcohol.

The term aspartame does not encompass physiologically acceptable salts of aspartame such as the hydrochloric acid salt (APM.HCl), but may include aspartame obtained from neutralization of such salts.

A method for crystallizing aspartame from aqueous solutions is described in U.S. Pat. Nos. 5,041,607 and 5,097,060, the complete disclosures of which are hereby incorporated by reference. According to this method, aspartame is substantially crystallized using conductive heat transfer for cooling without effecting forced flow, i.e. under conditions in which turbulence is avoided. This so-called static crystallization method requires special crystallization equipment and results in the formation of a hard, sherbet-like, pseudo-solid phase. Because of the limited method of cooling, it is not possible to obtain a heat transfer coefficient above approximately 100 $W/m^2.K$ on average during cooling, which means that the cooling time is relatively long. For example, it is believed that complete cooling and crystallization may take more than 3 hours in this process. Moreover, it has been found that aspartame crystals obtained by this static crystallization method are difficult to handle in a wet granulating process. The method yields unsuitable granulated products. These disadvantages of the prior art process are substantial.

In addition, a method for quickly cooling and crystallizing aspartame from aqueous solutions has been described in EP-A-0523813, the complete disclosure of which is hereby incorporated by reference. Cooling is achieved by direct contact of the aspartame solution with ice. However, the method is disadvantageous because cooling is not equally efficient throughout the whole aspartame solution and extensive dilution of the aspartame solution occurs due to the melting of large amounts of ice.

SUMMARY AND OBJECTS OF THE PRESENT INVENTION

Objects of the present invention include to provide a more rapid method for crystallizing aspartame.

A further object is to provide aspartame crystals having generally adequate crystal properties and having characteristics making them suitable for treatment in a wet granulating process.

A further object is to have equally efficient cooling throughout the whole aspartame solution.

A further object is to avoid dilution of the aspartame solution.

These and other objects are achieved in the present invention, which is a method for crystallizing aspartame comprising the combination of steps of:

providing (i) dispersed droplets of a fluid mixture comprising aspartame and water, and (ii) a water-immiscible fluid zone;

passing the dispersed droplets through the water-immiscible fluid zone under effective temperature and dispersive conditions to effect cooling of the dispersed droplets so that a metastable state of initial relative supersaturation of aspartame between about 1 and about 6 is formed within the dispersed droplets;

collecting the dispersed droplets in the supersaturated state in a substantially static collection zone so that a slurry comprising a crystalline form of aspartame is formed from the droplets.

The present invention is also for a method of crystallizing aspartame comprising the combination of steps of:

providing (i) dispersed droplets of a fluid mixture comprising aspartame and water at a first temperature and having a first density, and (ii) a water-immiscible fluid zone at a second temperature and having a second density, and having a viscosity of less than about 10 mPa.s, wherein the first temperature is at least 20° C. higher than the second temperature, wherein the first density is greater than the second density;

passing the dispersed droplets through the water-immiscible fluid zone so that nucleation in the droplets is substantially prevented and a metastable state of initial relative supersaturation between about 1 and about 6 is formed, collecting the dispersed droplets in the supersaturated state in a substantially static collection zone for sufficient time so that a slurry comprising a crystalline form of aspartame is formed from the droplets.

The process provides a rapid method for crystallization of aspartame yielding aspartame crystals of good quality and suitable for wet granulating treatment.

An unexpected result for the present invention is that when the crystalline aspartame product is obtained and dried, aspartame particles having a relatively smooth surface result. Surface smoothness can be determined, for example, by Scanning Electron Microscopy. In contrast, the crystalline aspartame product obtained by the state of the art static crystallization has a relatively rough surface. A relatively smooth surface is especially preferred when moistening of the product occurs such as, for example, during wet granulating. The dissolution rate of the crystals obtained according to the present invention may be slightly slower than the rate for crystals obtained by a static crystallization process. It is well known in the art, however, that the dissolution rate may be improved by further treatment of the crystals by, for example, reducing average particle size or adding dissolution rate enhancers.

DETAILED DESCRIPTION OF THE PRESENT INVENTION

Figure 1:
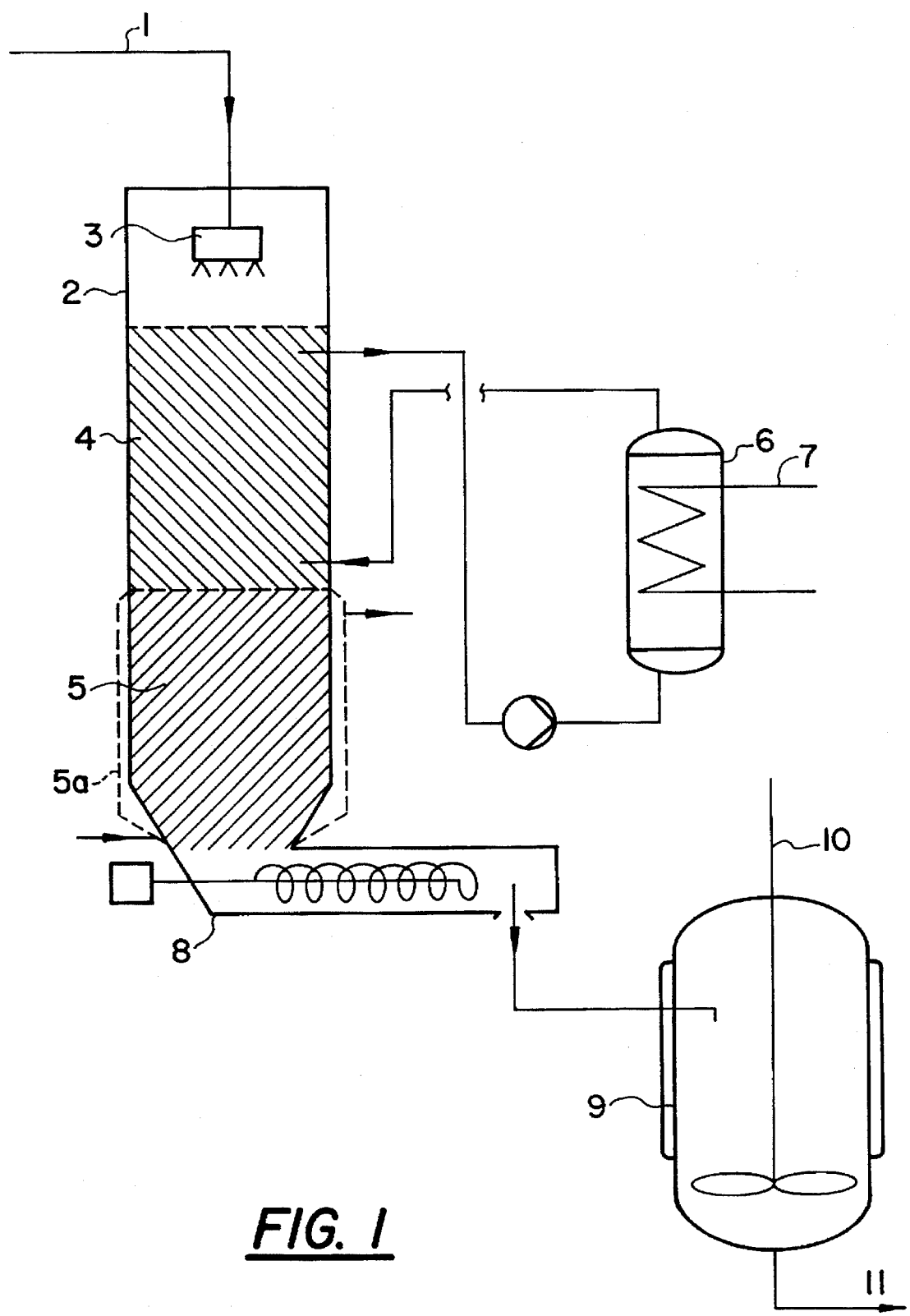
FIG. 1 provides a schematic diagram for an apparatus or a combination of devices used to effect the process according to the present invention.

In addition to aspartame, other products that show good crystallization behavior at high supersaturation may aim be crystallized according to the present invention. Preferably, however, aspartame is crystallized.

Relative supersaturation refers to a so-called metastable state before the start of crystallization. Initial relative supersaturation is defined by the ratio ($\sigma$)

$$\sigma = \Delta c/c^*.$$

wherein $\Delta c$ is the difference between the dissolved concentration of aspartame before crystallization starts and the saturated concentration of aspartame ($c^*$) in the mother liquor at the crystallization temperature.

The quantity, $c^*1$, as defined in this application, is calculated for solutions of aspartame in pure water in the temperature range of the slurries obtained in the present method according to the following formula:

$$c^* = 0.436 \times 10^{0.0177 T} \text{(in wt. \%)}$$

wherein T is temperature in °C. In the relevant temperature range, this formula is in good agreement with the formula described in Kishimoto et al., *A Process Development for the Bundling Crystallization of Aspartame*, J. Chem. Tech. Biotechnol., 43, 71 (1988), which provides the following formula at pg. 74:

$$c^* = 4.36 \times 10^{0.0177}(c^* \text{in g/l}; T \text{in °C.}).$$

The latter formula (using g/l), however, is less accurate than the former formula (using wt. %). Volume will change with temperature.

It is believed on the basis of present experimentation that the initial relative supersaturation should be between about 1 and about 6, and more preferably, between about 1.2 and about 4.

A fluid mixture comprising the material to be crystallized and water is prepared. The fluid mixture can, for example, comprise aspartame and an aqueous solvent. As already described, an aqueous solvent can be either water or a mixed solvent of water and up to about 25% (wt.) of a water-miscible organic solvent such as, for example, a $C_{1-3}$ lower alcohol. Moreover, the presence of a lower alcohol may be advantageous in later process steps such as, for example, removing solvent from the crystallized slurry under vacuum. The main advantage of using a mixed solvent, however, is that higher concentrations of dissolved aspartame can be achieved in the fluid mixture.

The water-immiscible fluid zone will in general comprise at least one liquid that is a poor solvent for aspartame so that the total water-immiscible fluid zone is a poor solvent for aspartame. Only minor amounts of water will be soluble therein.

The density of an aqueous solution of aspartame is dependent on the composition of that solution. The presence of a lower alcohol has a tendency to lower the density. In general, the density will be between about 0.95 and about 1.00 g/cm³ when measured at the temperature of the water-immiscible fluid zone.

The temperature difference between the hotter, aqueous aspartame droplets and the colder, water-immiscible fluid zone should be substantial. For example, the difference can be greater than or equal to about 20° C. This helps ensure that an acceptable yield of crystals is ultimately obtained. However, the temperature difference should not be too great such that an excessive burst of nucleation might occur in the droplets as they pass through the water-immiscible fluid zone. Undesired formation of small crystals might then result. In addition, temperatures greater than about 70° C. may result in decomposition of aspartame.

The dispersed droplets are, of course, cooled as they pass through the water-immiscible fluid zone. This cooling is an efficient process. The overall heat transfer coefficient for the cooling can be, for example, calculated to be between about 800 W/m².K and about 3,000 W/m².K. In contrast, the heat transfer coefficient for a conductive heat transfer cooling method, as described previously, is at best about 100 W/m².K. Experimental variables that effect the calculated heat transfer coefficient include the time it takes the droplets to pass the water-immiscible zone, the diameter of the droplets, and the temperature of the droplets during and immediately after passing the water-immiscible zone. A useful equation for calculation can be found in Perry and Green, *Perry's Chemical Engineers' Handbook*, VIth Ed. pg. 10–38, formula 10–147a, (1985), the complete disclosure of which is hereby incorporated by reference.

The fluid mixture comprising aspartame and water can be dispersed into droplets by various devices. Nozzle devices include, for example, spray nozzles, pressure nozzles, rotating nozzles, spinning atomizers, gas-atomizing nozzles, vibrating nozzles, or impact nozzles. Other exemplary devices include perforated plates or tubes, which are optionally vibrating. Still other devices include droppers and orifices.

The device for providing the dispersed droplets is generally placed near the upper liquid level of the water-immiscible fluid zone. The device for providing and dispersing droplets is in general relatively simple, inexpensive, and commercially available, and the skilled person will easily be able to determine which types are best suited for the purpose. Preferably, the dispersing device and method is selected to give reasonably uniform droplets: so-called monodisperse droplets. The average size of dispersed droplets can be adjusted over a wide range by the choice of dispersing conditions. Preferably, the range of droplet size will be relatively narrow.

In the most preferred embodiment, the apparatus or device for providing and dispersing droplets is placed a short distance from the surface of the water-immiscible fluid and is not in direct contact with the fluid. For example, the apparatus can be above the surface of the water-immiscible fluid. A lack of direct contact means that crystallization and/or dogging at the outlet of the dispersing device, such as a nozzle, is avoided. Such dogging might lead to undesired interruptions of the process. The distance between the dispersing means and the surface of the water-immiscible liquid is not believed to be critical, but usually, will not be more than about 2 meters to minimize equipment dead volume.

Depending on the geometry of the apparatuses and equipment used in the present invention, the upper surface level of the water-immiscible fluid zone in the equipment may rise during operation of the method of the invention. This would certainly occur, for example, during a batchwise operation when no withdrawal of crystallized slurry product takes place from the bottom of the crystallizing equipment. In a preferred embodiment, the dispersing droplet device or apparatus is vertically movable and can be adjusted in height throughout the process with respect to the position of the fluid. Such position adjustability of the dispersing device or apparatus is less important or may even be superfluous when the process of the invention is operated in a continuous mode, wherein the crystal slurry product is formed at one end (the bottom) of the water-immiscible fluid zone, while fresh aqueous aspartame solution is fed into the other end (the top) of the water-immiscible fluid zone. It is preferred that the dispersing of the droplets takes place at least 10 cm above the lower level of the water-immiscible liquid zone, in order to ensure that the dispersed droplets have sufficient cooling time while passing through the water-immiscible fluid zone. The minimum distance necessary for adequate cooling will depend on the droplet size.

For achieving good results, the temperature of the relatively hot aqueous solution of aspartame preferably should be at least 50° C. and the concentration of aspartame therein at least 2.5% by weight. If the temperature of the hot aqueous solution is lower than 50° C., the crystallization yield will be too low. Also, if the concentration of aspartame therein is too low, the relative supersaturation which can be achieved in the process of the invention also will be relatively low, and unfavorable results will be obtained. As stated above, the temperature difference between the relatively hot aqueous aspartame solution, which is at a first temperature, and the relatively cold water-immiscible fluid zone, which is at a second temperature, should be at least about 20° C. The temperature difference should be selected so as to ensure that no, or essentially no, nucleation occurs in the droplets as they pass through the water-immiscible liquid zone. The presence of nucleation can be visually observed, and if desired, examined in small scale experiments. Nucleation behavior may in some cases also be derived from crystallization/supersaturation curves, such as those presented in Kubota et at., J. Crystal Growth, 100, 491 (1990), the complete disclosure of which is hereby incorporated by reference.

Various experimental parameters such as, for example, temperature, droplet dispersion, and fluid selection can be, with guidance described herein, adjusted in an effective manner by a person of skill in the art to practice the process of the present invention. Depending on such things as the particular application and the experimental equipment, different parameters may be selected to achieve the proper state of nucleation and supersaturation.

Advantageously, the relatively low temperature of the water-immiscible fluid zone is held to an approximately constant temperature, despite heat transfer due to the passing of the relatively hot dispersed droplets. As the zone is warmed by the droplets, heat can be removed from the zone by cooling. Preferably, indirect cooling is used. Indirect cooling may be provided by: (1) cooling of the surface area of the part of the crystallizing vessel/tube containing the water-immiscible fluid zone, or (2) cooling by externally circulating at least some of the water-immiscible fluid through a heat-exchanger. The latter method of indirect cooling is preferably effected by counter-currently feeding and removing the water-immiscible fluid in such a way that essentially none of the dispersed droplets are entrained to the external heat exchanger. This can be achieved by an effective design of the equipment. For example, tangential feed lines and an overflow duct can be used.

The temperature of the coolant used for cooling the water-immiscible fluid zone usually will be between about −10° and about 20° C. The person of skill in the art can select conditions depending on factors such as, for example, the equipment, the temperature of the hot aqueous aspartame solution, and the temperature of the water-immiscible fluid zone.

The water-immiscible fluid can be circulated and externally cooled, preferably, by withdrawing fluid from the top or upper level of the water-immiscible fluid zone, with minimal entrainment of the droplets, and feeding the fluid counter-currently near the lower level of the liquid. It is advantageous to execute such withdrawal and feeding in such way that the basically stationary conditions in the crystallizing equipment are least disturbed. This can be achieved, for example, by use of baffles, tangential feeding, and the like, as known to those skilled in the art.

In theory, gradual gradients in properties of the water-immiscible fluid zone can be present. For example, a temperature gradient may be present. Gradients may, however, present complications.

In a preferred embodiment of the present invention, the water-immiscible fluid is contained in one or more tubular columns. Each column is preferably equipped with droplet dispersing means.

The dispersion of droplets should preferably occur at such a distance from the internal side-walls of the crystallizing equipment, especially in case one or more tubular columns are used, so that the droplets will essentially not come into contact with the side-walls while passing through the fluid. Contacts with the side-walls can result in long residence times for some of the droplets and undesired crystallization and scaling at the side-walls. The person of skill can select desirable configuration and design of the equipment.

The size and shape of the droplets can be diverse, but it is preferred that the size of the droplets can be approximately measured by a diameter between about 0.05 and about 5 mm, and most preferably, about 0.1 and about 3 mm on average. The best results are obtained if the droplets are monodisperse, i.e., have approximately uniform size or diameter. The size or diameter of the droplets is one of the factors influencing the cooling rate and the required time for the droplets to pass through the water-immiscible fluid zone. As the size or diameter of the droplet becomes smaller, the cooling rate will be faster. Usually, good crystal properties are obtained when droplets having a size or a diameter of about 0.1 to about 3 mm are dispersed. The person of skill in the art can select such factors as dispersion devices and methods, droplet size, water-immiscible fluid, and equipment so as to provide the most desirable results.

The water-immiscible fluid can be chosen from a wide range of fluids or liquids having a low or negligible solubility in water. The density of the fluid is preferably significantly lower than the density of the dispersed droplets at the same temperature. The density of the dispersed droplets, a first density, is greater than the density of the water-immiscible fluid zone, a second density. A significant difference of density is believed to be at least about 0.03 g/cm$^3$. The density of the fluid can be, for example, between about 0.5 and about 0.97 g/cm$^3$. Preferably, the fluid comprises a single or mixture of aliphatic or aromatic hydrocarbons having from 5 to 12 carbon atoms. The viscosity of the fluid can be, for example, between about 0.1 to about 10 mPa.s. Most preferably, the fluid comprises toluene or n-heptane.

Toluene, which has a density closer to that of water, has the advantage that the droplets falling into the liquid are dampened more effectively, so that their impact when reaching the lower aqueous crystallizing slurry is lowest and crystals formed or present in the lower part of the equipment are least affected. Heptane has the advantage that even less entrainment of organic liquid into the collection zone occurs, so that the crystallizing slurry of the collection zone is even more free of the water-immiscible fluid than in the case of toluene.

In general, however, the entrainment of water-immiscible fluid into the crystallizing slurry will be lower if the impact of the droplets onto the substantially static collection zone is lower. If the layer of water-immiscible fluid zone is not too thin, the impact is essentially independent of height of the water-immiscible fluid zone as the droplets pass therethrough at about linear speed. The linear speed can be described by the terminal settling velocity. Measuring the terminal settling velocity of the droplets offers opportunity for determining the droplet diameter, because the terminal settling velocity is related to diameter according to Stokes' law.

Preferably, in passing through the water-immiscible fluid zone, the droplets are cooled from a temperature of 50° C. or higher to a temperature in the range of about 35° C. to about 20° C., or even lower, such as about 15° C. If the aqueous solution also contains a lower alcohol, the aspartame concentration in the droplets may be higher. Hence, the start of nucleation will occur at a different relative supersaturation than when using water as the sole solvent for aspartame under otherwise identical conditions.

The time it takes for the dispersed droplets to pass through the water-immiscible fluid zone is called the effective time. The effective time is preferably between about 2 and about 60 seconds, and preferably, between about 5 and about 30 seconds.

The droplets, after having passed through the water-immiscible fluid zone, are collected at the other end of the crystallization equipment in a substantially static collection zone. Preferably, collection of the droplets occurs in a condition of low or negligible mechanical agitation or disturbance. Much of the nucleation and crystallization then takes place under these substantially static conditions. Optionally, the collected droplets may be cooled further by indirect cooling.

It is preferred that the average residence time of the aqueous phase collected in the bottom part of the equipment, while being kept without mechanical agitation or the like, is at least 30 minutes. During this time, a kind of network of aspartame crystals is formed. The network may be stronger or weaker depending on the amount of aspartame present, but if necessary, the network can be destroyed by mechanical treatment. The network formed according to the present invention is different from the so-called sherbet-like pseudo solid phase as is formed in static crystallization. The pseudo solid phase, when formed in a beaker, will retain all of the aqueous solvent when the beaker is turned upside-down.

The lower portion of the network of aspartame can be removed as a slurry without influencing the upper portion of the network of aspartame. Removal can be effected, for example, by continuous or batchwise use of a mechanical screw-feeder. Continuous operation is most preferred.

The overall process of the present invention may be operated in a batchwise, semi-continuous, or continuous mode. The latter two modes are preferred in view of industrial feasibility of the continuous process. The operation can be carried out advantageously by continuously withdrawing amounts of aspartame crystal slurry from the bottom part of the collected aqueous phase, either continuously or intermittently, after having remained there without mechanical agitation for at least 30 minutes on average.

As indicated above, optionally the collected droplets can be cooled further by indirect cooling. The further cooling can increase the yield of crystals. This may be done, for example, either by further cooling the substantially static collection zone of the crystallizing equipment, or by withdrawing crystal slurry therefrom to another vessel, which has been cooled to a lower temperature in the range of, for example, about 0°–20° C. Further crystallization can be carried out in this additional vessel. Preferably, the further crystallization is then effected while stirring because this increases the cooling rate and crystal output per unit of time. It was unexpected that this higher yield of crystals was obtained without negatively influencing crystal size and properties.

After crystallization of aspartame, optionally with further cooling, the collected droplets and the water-immiscible fluid zone are separated. Any water-immiscible fluid remaining in the collected droplets may be removed from it by methods known in the art such as, for example, evaporation.

The method of the present invention can be carried out in, for example, equipment as shown schematically in FIG. 1. In FIG. 1, which illustrates a preferred embodiment, the numerals mean: (1) represents the feedline through which a hot aqueous aspartame solution, which is prepared and kept at elevated temperature in a storage vessel (not shown), is fed from the top into a vessel or column (2), which is partially filled with the water-immiscible fluid forming a zone. This feeding occurs through a dosage system (3), comprising a device or apparatus for dispersing droplets. The dosage system may be, if desired, adjusted vertically in response to movements in the upper level of the water-immiscible fluid in the vessel. (4) represents the zone of water-immiscible fluid in vessel (2), whereas (5) represents the zone of collected droplets where most nucleation occurs and crystallization takes place. This zone optionally may be cooled by conductive heat transfer **(5*a*). The water-immiscible fluid may be circulated through an external cooler (6) for maintenance of an approximately constant temperature while the hot aqueous aspartame-containing droplets pass through the column. Undesirable entrainment of fluid mixture comprising aspartame and water to the external cooler (6), which is operated with a refrigerant (7), is avoided by appropriate positioning of the circulation lines and design of the vessel (2), e.g. by installing an overflow duct. At the bottom part of vessel (2)**, a device or apparatus is provided for discharging the slurry from the network formed from the collected droplets and transporting the slurry to another vessel (9), which is equipped with a stirrer (10) where optional further cooling may take place. The crystal slurry finally obtained is discharged through outlet (11) for use in further process steps for recovering and drying the aspartame crystals.

The present invention can be practiced with equipment and methods as schematically shown in FIG. 1. However, the equipment is not restricted or limited to the apparatus shown in FIG. 1, but may be comparable to extraction equipment and may have features of an extraction column for liquid-liquid extraction. The selection and construction of the equipment for use in the present invention is within the skill of the art.

A process for crystallizing aspartame by passing droplets comprising aspartame and water through a water-immiscible fluid has been described in Rijkers et al., EP application number 94203726.8, the complete disclosure of which is hereby incorporated by reference.

The present invention is now further illustrated in the following examples without being restricted thereto.

EXAMPLES

Almost all experiments were performed using glass equipment comprising a tubular column (height 75 cm; diameter 10 cm) having its middle equipped with a jacket through which coolant can be circulated. Above the column, a one liter feed vessel containing aqueous aspartame solution at elevated temperature was placed. The lower part of the column was provided with a discharge valve, through which the collected droplets could be discharged.

The starting solution was fed into the column dropwise either through a 0.9 mm syringe for obtaining droplets of about 3 mm in average diameter, or was pumped into the column through a nozzle for obtaining droplets of <0.5 mm in average diameter. The average droplet diameter was determined, for each type of experiment and hot solution used, either by counting droplets and weighing, or by measuring the terminal settling velocity according to Stokes' law. Both measuring methods give roughly the same result. At the start of each experiment, the column was filled with about 4 liter of water-immiscible fluid at a temperature about the same as that of the slurry temperature aimed at without additional cooling of the collection zone or slurry, and the experiment was continued until about 15 cm height (i.e. a volume of about 1 liter) of aqueous slurry was obtained in the bottom part of the column. The effective time is the time the falling droplets are passing through the water-immiscible liquid. Further residence times in the bottom part are not believed to be critical and are merely intended for ensuring completion of crystallization. The residence time is longer than the effective time.

During the experiments, the temperature gradient of the water-immiscible fluid was kept at a minimum by cooling the middle part of the water-immiscible fluid zone by circulating a coolant of appropriate temperature through the jacket. The temperature of the slurry obtained was continuously monitored by a thermometer placed in the bottom part of the column. It also was established that this slurry temperature was only slightly higher (at most 4° C.) than the temperature of the lower part of the water-immiscible fluid. Properties of the crystal slurries obtained were determined at the temperature of the slurry, after separating the slurry layer from the water-immiscible liquid layer, by determining the specific cake resistance at constant pressure difference, as described for example in EP-A-0399605, the complete disclosure of which is incorporated by reference. The determination was made based on the method b described in EP-A-0399605 in which the formula of Poiseuille and d'Arcy was used. The error in the measurement, after recalculation, is estimated to be about $1 \times 10^9$.

For purposes of better comparability, all specific cake resistance values are shown as determined or re-calculated at a pressure difference $\Delta p$ of 0.25 bar (25 kPa). For some of the slurries (of experiments 1, 2, and 3), cake compressibility was also determined (respectively being 0.56, 0.50 and 0.64, i.e. on average 0.57). This was done, according to standard methods, after determining the specific cake resistance at 5 chosen pressure differences.

The data or assumptions regarding cake compressibility are necessary for converting specific cake resistance values at various pressure differences. By measuring filtration characteristics at various pressure differences, a good assessment of the compressibility can be obtained. The following formula can be used:

$$\alpha_{\Delta p1}/\alpha_{\Delta p2} = (\Delta p1/\Delta p2)^a \text{ where } a = \text{compressibility}.$$

Here, $\alpha$ refers to specific cake resistance, and $\Delta p$ refers to pressure difference. Various information and conditions for the experiments are summarized in Table 1.

TABLE 1

| Exp/ Comp. | (C) with | Feed Compsn[2] | APM [Temp] | Slurry Temp. | concentration values (wt. %) and $\sigma$ | | | Droplet Size | Specfc Cake Rsstce (m/kg) |
|---|---|---|---|---|---|---|---|---|---|
| Exp | T/H[1] | Wt % | (°C.) | (°C.) | c* | $\Delta$c | $\sigma$ | (mm) | *10$^{-9}$)[3] |
| 1 | T | 4 | [65] | 23.5 | 1.09 | 2.91 | 2.67 | 0.1–0.5 | 1.9 |
| 2 | H | 4 | [65] | 22 | 1.03 | 2.97 | 2.88 | 0.1–0.5 | 2.3 |
| 3 | T | 4 | [65] | 22.5 further stirred cooling to 10.5 | 1.05 | 2.95 | 2.81 | 0.1–0.5 | 1.7 |
| 4 | H | 4 | [65] | 24.2 | 1.12 | 2.88 | 2.57 | 2.5–3 | 5.6 |
| C.1 | H | 6 | [68] | 10.5 | 0.66 | 5.34 | 8.09 | 2.5–3 | 34.0 |
| 5 | H | 4 | [64] | 34.2 | 1.66 | 2.34 | 1.41 | 2.5–3 | 5.7 |
| C.2 | H | 3 | [62] | 35.0 | 1.72 | 1.28 | 0.74 | 2.5–3 | 31.0 |
| 6 | H | 6 | [68] | 35.0 | 1.72 | 4.28 | 2.49 | 2.5–3 | 1.2 |
| 7 | H | 3 | [62] | 24.5 | 1.14 | 1.86 | 1.63 | 2.5–3 | 5.3 |

TABLE 1-continued

| Exp/ Comp. | (C) with | Feed Compsn[2] | APM [Temp] | Slurry Temp. | concentration values (wt. %) and σ | | | Droplet Size | Specfc Cake Rsstce (m/kg |
|---|---|---|---|---|---|---|---|---|---|
| Exp | T/H[1] | Wt % | (°C.) | (°C.) | c* | Δc | σ | (mm) | *10⁻⁹)[3] |
| 8 | H | 6 | [68] | 25.5 | 1.18 | 4.82 | 4.08 | 2.5–3 | 4.6 |
| 9 | H | 6 H₂O/MeOH | [66] | 22.5 | 1.20 note[4] | 4.80 | 4.00 | 0.1–0.5 | 2.8 |

[1]T/H refers to the water-immiscible solvent used in the column: T = toluene; H = n-heptane. Experiment 9 (APM solution in water/reethanol) was performed in a column having a diameter of 8 cm. The flow-rate of the feed solution was 1.15 kg/hour in expt. 9.
[2]All experiments, except exp. 9, were performed with use of APM in pure water. In experiment 9, however, a mixed water/methanol solvent was used (1480 g water and 400 g methanol).
[3]All values, except for comp. expt. 1 and for expt. 9, were determined at a pressure difference of 0.25 bar (25 kPa). For comp. expt. 1 and expt. 9 determination occurred at a pressure difference of 1 bar (100 kPa), but the value shown in the Table has been re-calculated to the value for 0.25 bar (taking the compressibility at 0.57).
[4]Determined using data from EP-A-0128694

In Table 1, the first column shows the number of the Experiment or Comparative experiment (C.) The first column also indicates the water-immiscible solvent used: T for toluene and H for n-heptane. The second column relates to the feed solution and shows the APM-content (in wt. %) and temperature (in °C.). Experiment 9 was carried out using water/methanol as solvent, whereas all other experiments were carded out with use of pure water as solvent. In experiment 3, the slurry obtained was further cooled with agitation to 10.5° C. before cake resistance was determined. The temperatures of the slurries obtained are shown in the third column. Column 4 shows the pertinent data for c*, Δc and σ; σ follows from the formula σ=Δc/c*. Column 5 shows the droplet size (diameter) in mm, and column 6 shows the specific cake resistance values at 25 kPa (for instance, "1.9" means "$1.9*10^9$m/kg").

In the present invention, aspartame crystals with good properties are obtained in a process with efficient and rapid cooling. Comparative experiments 1 and 2, which were performed at an initial relative supersaturation of 8.09 and of 0.74, respectively, clearly yield poor results in specific cake resistance values.

In addition, the products obtained according to the present invention, after filtering, can be easily handled in a wet granulating process. Achieving equally favorable handling in wet granulation is believed to be impossible for aspartame crystallized by static crystallization according to the aforementioned U.S. Pat. Nos. 5,041,607 and 5,097,060. This method yields unsuitable granulated products.

Wet granulation tests were performed in an Eirich granulator comprising a 5 dm³ rotating vessel positioned at an angle of 30° from vertical and having an internal rotor rotating in opposite direction. The vessel was rotated at a rotation speed of 42 rpm, while the tip speed of the rotor was 2.8 m/sec. The water content of the starting product for wet granulation was about 60%, and during the granulation process, this water content was lowered to about 30% by passing a stream of air at 65° C. over the product layer. Granulation began when the water content of the product was about 45–40 wt. % or lower. Particle size distribution, bulk density, and friability of the granular products obtained were determined, as well as their potential for mechanical compaction. Friability is a measure of resistance against particle attrition. Higher values of friability show less resistance: more dust formation occurs during the testing for friability. Such tests can be performed in, for example, rotary drums and, optionally, with the use of solid bodies moving within the drum.

Aspartame crystals made by the method of the present invention could be granulated in about 4–5 hours to obtain granular products having properties as shown below.

The data given below in square brackets indicate properties of granular aspartame crystallized according to the comparative methods described in U.S. Pat. Nos. 5,041,607 and 5,097,060. This method produces unsuitable granulated products. In the comparative experiments, the moisture content at the start of this experiment was 32 wt. %, and wet granulation was possible without adding more water. Due to the lower water content, granulation was faster (about 2 hours), and final moisture content was about 23%. However, the products of wet granulation from the comparative process were not suitable.

| Particle size distribution (psd. in mm). | |
|---|---|
| $d_{10}$ 0.6–0.8 | [<0.02] |
| $d_{50}$ 2.0–3.0 | [0.05] |
| $d_{90}$ 3.0–8.9 | [0.56] |
| Friability (in %: should be <20): | |
| 6–10 | [60] |
| Max. tablet density (in kg/m³): | |
| 1000–1080 | [1120] |
| at a max. pressure of (in kN/cm²): | |
| 9–11 | [10] |
| with max. tablet strength (in N/cm²): | |
| 330–420 | [170] |

While the invention has been described in detail and with reference to specific embodiments thereof, it will be apparent to those of ordinary skill in the art that various changes and modifications can be made therein without departing from the spirit and scope thereof.

What is claimed is:

1. A method of crystallizing aspartame comprising the combination of steps of:
   providing (i) dispersed droplets of a fluid mixture comprising aspartame and water, and (ii) a water-immiscible fluid zone;
   passing said dispersed droplets through said water-immiscible fluid zone under effective temperature and dispersive conditions to effect cooling of said dispersed droplets so that a metastable state of initial relative supersaturation of aspartame between about 1 and about 6 is formed within said dispersed droplets and;

collecting said dispersed droplets in said supersaturated state in a substantially static collection zone so that a slurry comprising a crystalline form of aspartame is formed from said droplets.

2. A method according to claim 1, wherein a device for providing said dispersed droplets is near an upper level of said water-immiscible fluid zone.

3. A method according to claim 2, wherein said device for providing said dispersed droplets is a short distance above but not in direct contact with said upper level of said water-immiscible fluid zone.

4. A method according to claim 2, wherein said device can move with respect to said upper level of said water-immiscible fluid zone during said crystallizing of aspartame.

5. A method according to claim 1, wherein said dispersed droplets are provided at least about 10 cm above a lower level of said water-immiscible fluid zone.

6. A method according to claim 1, wherein a temperature of said fluid mixture is at least about 50° C. and a concentration of said aspartame in said dispersed droplets is at least about 2.5 wt. %.

7. A method according to claim 1, wherein said water-immiscible fluid zone is indirectly cooled.

8. A method according to claim 1, wherein at least some of said water-immiscible fluid zone is circulated and externally cooled by withdrawing at least some of said fluid zone from near an upper level of said water-immiscible fluid zone, without entrainment of said fluid mixture comprising aspartame and water, and feeding said withdrawn fluid zone countercurrently back into said water-immiscible fluid zone near a lower level of said water-immiscible fluid zone.

9. A method according to claim 1, wherein said water-immiscible fluid zone is contained in at least one tubular column.

10. A method according to claim 9, wherein said dispersed droplets do not come into contact with a side-wall of said tubular column as said dispersed droplets pass through said water-immiscible fluid zone.

11. A method according to claim 1, wherein said dispersed droplets, as provided, have an approximate diameter between about 0.05 mm and about 5 mm.

12. A method according to claim 1, wherein said water-immiscible fluid zone comprises a $C_5$–$C_{12}$ aliphatic hydrocarbon liquid, a $C_5$–$C_{12}$ aromatic hydrocarbon liquid, or a mixture thereof.

13. A method according to claim 1, wherein said water-immiscible fluid zone comprises toluene or n-heptane.

14. A method according to claim 1, wherein said dispersed droplets cool to a temperature between about 20° C. and about 35° C. while passing through said water-immiscible fluid zone.

15. A method according to claim 1, wherein said substantially static collection zone is indirectly cooled.

16. A method according to claim 1, wherein said slurry is kept without mechanical agitation for at least about 30 minutes.

17. A method according to claim 1, wherein a bottom part of said slurry is removed from said substantially static collection zone without substantially disturbing an upper part of said slurry.

18. A method according to claim 17, wherein said bottom part of said slurry is removed continuously or intermittently.

19. A method according to claim 18, wherein said removed bottom part of said slurry is cooled to a temperature between about 0° C. and about 20° C.

20. A method according to claim 1, wherein said water-immiscible fluid zone and said slurry are separated, and any water-immiscible fluid remaining in said slurry is removed.

21. A method of crystallizing aspartame comprising the combination of steps of:

providing (i) dispersed droplets of a fluid mixture comprising aspartame and water at a first temperature and having a first density, and (ii) a water-immiscible fluid zone at a second temperature and having a second density, and having a viscosity of less than about 10 mPa.s, wherein said first temperature is at least 20° C. higher than said second temperature, and wherein said first density is greater than said second density;

passing said dispersed droplets through said water-immiscible fluid zone so that nucleation in said droplets is substantially prevented and a metastable state of initial relative supersaturation between about 1 and about 6 is formed, collecting said dispersed droplets in said supersaturated state in a substantially static collection zone for sufficient time so that a slurry comprising a crystalline form of aspartame is formed from said droplets.

22. A method according to claim 1, wherein said crystalline form of aspartame is collected to yield crystals having specific cake resistance of less than about $25 \times 10^9$ m/kg.

* * * * *